US009417214B2

(12) United States Patent
Loeser et al.

(10) Patent No.: US 9,417,214 B2
(45) Date of Patent: *Aug. 16, 2016

(54) APPARATUS FOR DETERMINING THE TEXTURE OF FOOD MATERIAL

(71) Applicant: Kraft Foods R & D, Inc., Northfield, IL (US)

(72) Inventors: Ulrich Loeser, Sauerlach (DE); Erich J. Windhab, Hemishofen (CH); Stefan Padar, Lupsingen (CH); Bruno Pfister, Hüntwangen (CH)

(73) Assignee: Kraft Foods R & D, Inc., Deerfield, IL (US)

( * ) Notice: Subject to any disclaimer, the term of this patent is extended or adjusted under 35 U.S.C. 154(b) by 400 days.

This patent is subject to a terminal disclaimer.

(21) Appl. No.: 14/049,651

(22) Filed: Oct. 9, 2013

(65) Prior Publication Data
US 2014/0033819 A1 Feb. 6, 2014

Related U.S. Application Data

(63) Continuation of application No. 12/361,900, filed on Jan. 29, 2009, now Pat. No. 8,567,250.

(30) Foreign Application Priority Data

Feb. 1, 2008 (EP) ..................................... 08001905

(51) Int. Cl.
*G01N 9/24* (2006.01)
*G01N 29/22* (2006.01)
(Continued)

(52) U.S. Cl.
CPC .............. *G01N 29/22* (2013.01); *G01N 29/036* (2013.01); *G01N 29/222* (2013.01); *G01N 29/2437* (2013.01); *G01N 29/30* (2013.01); *G01N 29/4436* (2013.01); *G01N 33/02* (2013.01); *G01N 2291/014* (2013.01);
(Continued)

(58) Field of Classification Search
None
See application file for complete search history.

(56) References Cited

U.S. PATENT DOCUMENTS 2,508,152 A    5/1950   Friedman
5,152,401 A   10/1992   Affeldt, Jr. et al.

(Continued)

FOREIGN PATENT DOCUMENTS

CN       1709075 A       12/2005
DE    2 132 206 A1        1/1973

(Continued)

OTHER PUBLICATIONS

Alexandre I. Romoscanu et al., "High Frequency Probe for the Measurement of the Complex Viscosity of Liquids," Measurement Science and Technology 14 (2003) 451-462.

(Continued)

*Primary Examiner* — Robert R Raevis
(74) *Attorney, Agent, or Firm* — Fitch, Even, Tabin & Flannery LLP

(57) ABSTRACT

The present application relates to an apparatus for determining the texture of food material, wherein the apparatus comprises a device for generating a vibrational impact, such as a piezo actuator, a device for measuring vibrations, such as a vibrometer, a holding mechanism, comprising a container body for containing the food material therein or a string to attach the food material thereto, and an analyzer for comparing measured vibrations with at least one reference value, determined prior to the measurement.

17 Claims, 5 Drawing Sheets

(51) Int. Cl.
*G01N 29/036* (2006.01)
*G01N 29/24* (2006.01)
*G01N 29/30* (2006.01)
*G01N 29/44* (2006.01)
*G01N 33/02* (2006.01)

(52) U.S. Cl.
CPC ... *G01N 2291/022* (2013.01); *G01N 2291/024* (2013.01); *G01N 2291/0252* (2013.01)

(56) References Cited

U.S. PATENT DOCUMENTS

| | | |
|---|---|---|
| 5,691,473 A | 11/1997 | Peleg |
| 5,811,680 A | 9/1998 | Galili et al. |
| 6,276,536 B1 | 8/2001 | Terasaki et al. |
| 6,894,178 B1 | 5/2005 | Windhab et al. |
| 6,912,891 B2 | 7/2005 | Coupland et al. |
| 6,948,379 B2 | 9/2005 | Hussain et al. |
| 7,028,529 B2 | 4/2006 | Gessert et al. |
| 7,214,319 B2 | 5/2007 | Yen et al. |
| 7,240,553 B2 | 7/2007 | Segura et al. |
| 7,562,557 B2 | 7/2009 | Bennett et al. |
| 7,691,928 B2 | 4/2010 | Sato et al. |
| 2004/0112121 A1 | 6/2004 | Kornfeldt et al. |
| 2005/0112255 A1 | 5/2005 | Tottenham et al. |
| 2006/0182863 A1 | 8/2006 | Mori et al. |

FOREIGN PATENT DOCUMENTS

| | | |
|---|---|---|
| DE | 43 14 553 A1 | 11/1994 |
| EP | 0 577 511 A1 | 1/1994 |
| KR | 2002-0025570 A | 4/2002 |
| RU | 2 031 592 C1 | 3/1995 |
| RU | 2 060 672 C1 | 5/1996 |
| RU | 2 151 518 C1 | 6/2000 |
| SU | 845031 A1 | 7/1981 |
| SU | 1424784 A1 | 9/1988 |
| SU | 1544342 A1 | 2/1990 |
| SU | 1762854 A1 | 9/1992 |
| WO | 89/04463 A1 | 5/1989 |
| WO | 01/94933 A1 | 12/2001 |

OTHER PUBLICATIONS

Jiri Blahovec et al., "Laser Doppler Forced Vibrology of Soft Agricultural Products," Applied Rheology 17(2) (2007) 25111-1-25111-7.

European Patent Office Extended European Search Report for European Patent Application No. 08001905.2 dated Oct. 9, 2008, 6 pages.

APPARATUS FOR DETERMINING THE TEXTURE OF FOOD MATERIAL

CROSS-REFERENCE TO RELATED APPLICATIONS

This application is a continuation of prior application Ser. No. 12/361,900, filed Jan. 29, 2009, which claims priority from European Application Number EP 08001905.2, filed Feb. 1, 2008, which are both hereby incorporated herein by reference in their entirety.

FIELD OF THE INVENTION

The invention relates to a method of determining the texture of food material by measuring its vibrational response to a controlled vibrational impact. An apparatus for use in this method is also provided.

BACKGROUND ART

It is known in the art to use vibration measurement techniques to determine the mass flow of a gas or a liquid. When a tube through which fluid material flows is made to oscillate in a direction perpendicular to that of the flow, Coriolis forces will act on the tube. Measurement of the tube displacement due to these forces then allows for the mass flow to be quantified. A mass flow meter based on this Coriolis principle is disclosed for example in WO 89/04463. The apparatus described therein comprises a throughflow device, such as a tube or a pipe, an exciter device and a plurality of sensor elements, arranged at different positions on the throughflow device. When there is fluid flow through the apparatus, the exciter device is used to oscillate the throughflow device and the oscillations are monitored with the sensor elements. The Coriolis forces occurring due to the material flow cause a phase shift between the oscillations at different locations on the throughflow device. The magnitude of this phase shift is determined using two sensor elements placed at different positions and provides a direct measure of the mass flow through the device. In addition, such mass flow meters may also be used to quantify the density of a fluid in flow, since the resonance frequency of the throughflow device is dependent on the mass of the flowing material. However, the above described method is limited to gaseous or liquid materials and does not offer any information on material texture.

In Applied Rheology 17, 25111-1-25111-7 (2007), the method of laser Doppler forced vibrology applied to soft agricultural products is described. In this measurement technique, a solid food product, such as a melon, is placed on a vibration generator, e.g., a vibrating table, and thus caused to oscillate. The oscillations of the product induced in this way are investigated by measuring its surface motion with a laser Doppler vibrometer. Analysis of the resonance peak frequencies yields the modulus of elasticity of the product which may be helpful to evaluate the product quality, maturity or firmness.

In Measurement Science and Technology 14 (2003) 451-462, a rheological measurement set-up comprising a tube section with a pair of magnets attached to it and a pair of coils fitted on a supporting frame is used to investigate the flow properties of liquids. The tube section containing the flowing liquid is electromagnetically driven to torsionally oscillate, using the magnet/coil pair as an actuator and the oscillatory response of the tube is subsequently picked up by the same magnet/coil pair. The phase shift between the driving signal and the response signal is measured and used to determine the resonant frequency and the damping of the liquid sample. Subsequently, the complex viscosity of the liquid is determined from these latter two parameters with the help of a theoretical model.

SUMMARY OF THE INVENTION

The first objective of the invention is to provide a reliable non-destructive and non-invasive method of determining the texture of food material. In a second aspect, the invention aims to provide an apparatus for employing said method. These goals are achieved by a method with the technical features of claim 1 and an apparatus with the technical features of claim 15. Preferred embodiments of the invention follow from the subclaims.

The invention provides a method of determining the texture of food material, comprising the steps of applying at least one vibrational impact (such as an oscillating excitation, a sound impact or any kind of impact that serves to oscillate or "shake" the food material) with a frequency within a predetermined frequency range and with a predetermined time-length to the food material, measuring the vibrational response (such as a displacement, movement, oscillation etc. of the food material) of the food material to the at least one vibrational impact, and comparing the vibrational response with at least one reference value, determined prior to the measurement. Herein the term "texture" refers to the physical and/or chemical properties (or structure) of the food material to be investigated, including, but not limited to firmness, density, viscosity, elasticity, crystalline structure, homogeneity (e.g., coexistence of different phases or crystalline structures), chemical composition, molecular structure (microstructure) and the like. The food material to be investigated is in a liquid or a semi-solid state and/or contained within a container body, such as a pipe. If a measurement is performed on a food material contained within a container body, the food material may be stationary during the measurement, i.e., not in motion (e.g., flow) with respect to the container body. To measure said vibrational response, a single sensor device may be sufficient. The measurement of the vibrational response may include, for example, measuring the vibrational frequency and/or magnitude. The reference value may be determined prior to the measurement, for example by measuring a substance with a well-known texture or by measuring the food material to be examined for a certain set of well-defined outer parameters, such as temperature or pressure. The vibrational response depends on a variety of food material parameters, such as viscosity, density or consistency (e.g., coexistence of different phases in the material). The method of the invention may thus be applied to monitor food solidification processes, for example in a semi-solid food material as result of exposure to cooling or compression, by detecting changes in the texture as changes in the vibrational response of the material. In this way, incomplete food solidification can be identified and avoided, by adjusting the cooling time and/or temperature, for example in a cooling tunnel or even changing the design of such a cooling tunnel. Thus, the method described herein can be applied in at least two ways. Firstly, a fabrication process may be monitored "online". Secondly, the method described herein may be used to determine the texture of food material with varying process parameters and/or machine designs and/or similar parameters. The results obtained by the method described herein may then be used to decide about appropriate process parameters, machine designs or similar factors.

On the other hand, the solidification behaviour of a food material over time may offer valuable information on material quality and firmness. In this case, it is sufficient to measure while the food is still in a semi-solid state, without the need to wait for full crystallisation of the material. The method of the invention thus provides a tool to determine the quality of a food product in advance, before it is fully finished.

The measurement is non-destructive and non-invasive and thus does not cause any damage to the investigated food material. Hence, the method may be used for a quality test of finished food products or for controlling food properties during the production process. In the former case, the method may be employed, for example, to examine filled confectionery, like chocolate coated biscuits. Such a measurement can reveal important information on the condition of the product, e.g., whether the coating is complete and uniform or whether the biscuit was damaged in the production process (for example formation of cracks, incomplete lamination between two materials). In the latter case, fluctuations in texture or consistency can be immediately identified and compensated for, by adapting the appropriate parameters of the production equipment, such as temperature or pressure. In this way, a smooth operation of the production line especially at high operation line speed can be maintained. Close control of the food parameters is particularly important when the production process involves a step of combining different food components with varying texture and/or consistency, in order to achieve a desired component ratio. This is the case, for example, in the so-called "one-shot technology" in confectionery, where all constituents are deposited at the same stage of production and for example a 50% filling share should be achieved, maintained for flat tablets made within one step at ribbon depositing mode (where oblong filled confectionery products are produced by lateral movement of a food extrusion nozzle while the food material is being deposited by the nozzle), running permanently at top speed level and using unfavourable combinations of recipes (i.e., filling and coating materials with different textures and/or flow properties). In addition, the above method may also be used to identify different levels of gas inclusions in liquid or solid food material, e.g., during the de-aeration process of chocolate. The method of the invention can be applied to a large variety of food materials, such as cream cheese (e.g., for getting the right level of creaminess), sauces, dressings, any kinds of emulsions or suspensions, any liquids, solid or liquid nanostructures, semi-nanostructures, bakery products (e.g., for monitoring the properties of the dough) or spreads but may be further extended, for example, to cosmetics, such as lotions or creams, or pharmaceuticals.

The use of a container body is particularly advantageous for temperature or pressure dependent studies, since it allows for a precise control of these external parameters. For example, the container may be connected to a cooling or heating device.

In an embodiment of the invention, a plurality of vibrational impacts with varying predetermined frequencies and with a predetermined discrete time-interval is applied to the food material and the vibrational response of the food material to each of the vibrational impacts is measured. In this way, the accuracy of the method is improved, allowing for the detection of small changes in vibrational response.

The method of the invention may further comprise a step of determining the resonant mode frequencies and magnitudes of the food material. Changes in the food material texture will affect the frequencies or the magnitudes of the resonant modes of the food material, or both of these parameters. By monitoring the two parameters, the measurement accuracy can thus be optimised. The measurement process may consist of applying vibrational impacts with varying predetermined frequencies to the food material, measuring the vibrational response of the food material to each of the vibrational impacts and plotting the oscillation magnitudes of the vibrational responses versus the vibrational response frequencies. Herein, the vibrational response frequencies and magnitudes may be extracted from the data as measured by employing a Fourier transformation analysis method. In such a frequency-magnitude plot, the resonant mode peaks can be identified and their height and position can be determined. In addition, the resonance peak linewidth (e.g., full width at half maximum) can be extracted from the plot, providing further information on the vibrational response, in particular the damping of the respective vibrational mode, and thus the texture of the investigated food material. A comparison of such plots at different times, temperatures, pressures, different thermal histories or different positions in the production line will then reveal changes in the food material texture. In particular, the result of such a comparison will not be dependent on factors such as the current temperature of the food material if it is well controlled. Rather, accurate information regarding the texture will be obtained. Furthermore, the plots may be compared to plots of materials with well-known texture parameters.

When the food material is contained within a container body, such as a pipe, the vibrational impact may, in a further embodiment, be applied to the container body and/or the vibrational response of the food material may be measured by measuring the displacement of the container body (e.g., a linear displacement or motion of the container body). Such a configuration is particularly useful for the investigation of liquid food. Furthermore, when for example a pipe or a tube is used as a food container, the texture of the food material may be measured in flow. The container may have movable parts, such as membranes, attached to or integrated in its walls, that may serve to apply a vibrational impact to the food material or to measure the vibrational response of the food material. Moreover, the vibrational impact may be applied directly to the food material and the vibrational response of the food material may be measured by measuring the displacement of the container body. On the other hand, the vibrational impact could also be applied to the container body and the vibrational response of the food material could be measured directly at the food material.

The investigated food material may be chocolate. In the procedure of chocolate "tempering", wherein the fat phase of chocolate mass (mainly in the cocoa butter) undergoes a phase transition from the liquid to the solid state (in contradiction to tempering with seeds, the traditional tempering process uses solely cooling and shearing to form crystals), a careful control of the cooling process is vital in order to achieve the desired fat crystal structure and concentration. Most fats, such as cocoa butter, are polymorphic and can crystallise in a number of different forms with varying stability as well as physical and chemical properties. In the case of tempered chocolate, various different crystalline structures (or forms) are present in the fat phase of the material depending on its thermal history.

To date, the presence of these different structures is usually detected by X-ray diffraction in a non-destructive and non-invasive manner. However, use of the X-ray diffraction method is normally limited to a lab environment. Furthermore, this method does not allow measurements on real chocolate, since sugar crystals in the chocolate diffract X-rays in the same region as the fat crystals. The present invention offers an alternative approach that permits to overcome this problem in that it allows for an investigation of the chocolate material texture at any point of time during the phase transition without the need to disturb the tempered mass or to make complicated preparations.

Two other methods utilise response signals after exposure of the samples to different temperature-time regimes using completely unequal measuring principles. They are named DSC (Differential Scanning calorimetry) and measurement of temper curves.

In this case, the DSC method is usually applied under lab conditions and delivers changes of enthalpy (ΔH) during cooling at a defined cooling rate and subsequent heating at a defined heating rate (ΔT/Δτ; where ΔT is the change in temperature for a given time interval Δτ). In this way, the DSC method allows to associate melting peaks with a certain temperature range. Information gained on the crystalline structures is limited to temperatures and enthalpy differences as a result of melting the crystalline phase. No further information about textures can be deduced from such measurements.

Measuring temper curves is widely used in confectionery operation. A sample is exposed to isothermal conditions, cools down and the temperature is recorded. The resulting temperature slope delivers a so-called temper index (over-tempered, well tempered, under-tempered, not tempered) and an inflection point in ° C. batch-wise. No information about crystalline structures or textures can be deduced from such measurements.

In particular, the method of the invention can be used to monitor the texture changes of such a tempered mass at almost constant processing temperatures, allowing for appropriate adjustments in the tempering machine of cooling time or temperature. The method of the invention is complementary to the existing above-mentioned measurement techniques of temper degree. Moreover, the method may be applied in production lines where liquid chocolate is processed, in order to maintain a steady flow of the chocolate mass, because the formation of new inner texture can also be identified in case of no flow. Furthermore, the food material may also be a compound or an enrobing mass or a confectionery filling mass. As described above, when different food components with varying texture (e.g., viscosity, density and/or consistency) are combined with each other in the process of food production, the method of the invention can be applied to achieve a desired component ratio, e.g., in the "one-shot technology" in confectionery. On the other hand, when coated food products are investigated, the method may be used to reveal information on the quality of the coating, such as completeness, presence of cracks and/or thickness uniformity.

In another embodiment, the investigated food material may have a nanostructure. In this case, the material may be in a semi-solid state with gaseous or liquid inclusions on the nanometer scale. On the other hand, the food material may also be a nanoliquid (nanofluid), such as for example a liquid with nanoparticles dispersed in it. The present method can be applied to detect the presence of such an ultra-small structure and to gain information on its details, which is difficult (or impossible) to achieve with conventional techniques, without disturbing or even damaging the material.

Further, the method of the invention may be used to monitor a de-aeration process of the food material. For example, during the fabrication of chocolate, air might easily get trapped in the liquid or semi-solid mass, e.g., in the process of stirring or shaking the material. The trapped air (or other gas, depending on the specific production conditions) may form bubbles that either remain in the bulk of the chocolate material, leading to a decrease in the mass of the finalised product, or rise to the chocolate surface, causing a roughening thereof. Thus, it is crucial for the fabrication of a high quality product to minimise such gas inclusions to a tolerable level, for example in case of a high pressure treatment to achieve improved microbiological stability. However, using conventional techniques, it is impossible to determine with a sufficient degree of accuracy the amount of air (or other gas) trapped in a food material, without severely interfering with the production process. This goal can be achieved with the method of the present invention. In this case, it is particularly advantageous, that the measurement may be carried out during the fabrication process, while the food material is still in a liquid or semi-solid state, without the need to wait for complete solidification of the product. Hence, the final production steps (e.g., tempering in the case of chocolate production) may only be carried out, once an acceptable level of de-aeration is achieved. On the other hand, the method of the invention may be applied before the fabrication process, in order to determine appropriate process parameters for achieving a finished product with a desired amount of gas inclusions. However, the present method is not limited to fabrication procedures where the level of gas inclusions in the food material is to be kept at a minimum but may be extended to the investigation of food material for which a controlled formation of gas inclusions is intended, such as chocolate with embedded air bubbles, in terms of micro-scale aerated gas. In this case, the method may be used to monitor for example the size and distribution of the gas bubbles in order to ensure a desired food texture.

In a currently preferred embodiment, the food material is stationary during the measurement, i.e., not in motion (e.g., flow) with respect to the measurement set up (such as the container body, if present). Hence, the method of the invention may be used in a batch-wise application. Also, the method according to the present embodiment may be used to investigate the texture of food material at various positions within a production line. In this case, the food material to be tested can be retained and isolated from external influences, e.g., by closing appropriate valves incorporated in the tubes or pipes of the production line. Such a measurement procedure can be performed at different times and positions in the production line, allowing for a close control of the food material texture.

In yet another embodiment, when the food material is in a liquid state and contained within a container body, such as a pipe, the food material may be in flow through the container body. Whilst, as stated above, applying the present method to stationary food material is currently preferred, such an embodiment of the invention can be beneficial. For example, the above method may be used to monitor the food material flow in a production line. Any fluctuations in texture or consistency can then immediately be identified and the production equipment can be re-adjusted accordingly, so as to guarantee an even output in product quality at high operation line speed. The deposition process can be re-started, once the desired texture formation is accomplished.

The flow direction of the food material may be substantially perpendicular to the direction of applied vibrational impact and to the measurement direction of the vibrational response of the food material. This geometry allows for a convenient and effective measurement, in particular, when the measurement equipment is integrated in a production or processing line.

The frequency of the applied vibrational impact may lie within a range of 0-20 kHz, preferably within a range of 0-10 kHz. In this frequency range, vibrational impacts can be generated by conventional methods, preferably by using a piezo actuator, and the vibrational response of the food material may be measured using standard means, preferably a vibrometer. Hence, the equipment costs can be kept at a reasonably low level. Furthermore, the use of a piezo actuator in combination with a vibrometer allows for a simple measurement set up, that can be easily assembled and incorporated into a production or processing line, without affecting the surrounding equipment.

The method according to the invention may further comprise a calibration step prior to the measurement. This calibration step can be performed without or with sample material. The measurement set up may be calibrated by measuring a "calibration substance" with well-known material parameters, such as viscosity and consistency, or by measuring the food material to be investigated for a certain set of well-defined external parameters, such as pressure or temperature.

In a second aspect, the invention provides an apparatus for determining the texture of food material, the apparatus comprising a device for generating a vibrational impact, such as a piezo actuator, a device for measuring vibrations, such as a vibrometer, a holding mechanism and an analyser for comparing measured vibrations with at least one reference value, determined prior to the measurement. The holding mechanism comprises a container body for containing the food material therein (such as a pipe or a tube) or a string to which the food material can be attached. The latter configuration may be used, for example, for the investigation of a semi-solid food material, e.g., during a solidification process.

In an embodiment, in the analyser the resonant mode frequencies and magnitudes of the food material are determined and compared.

In another embodiment, the holding mechanism comprises a container body for containing the food material therein that is made of a robust material, preferably a metal, such as stainless steel. A container body made of such a material has the advantage that it is stable within a wide range of temperatures and pressures, allowing for a detailed study of the food material properties for varying external conditions. This feature can be particularly important for tracking partial solidification processes.

In another embodiment, where the holding mechanism comprises a container body for containing the food material therein, the apparatus further comprises a sensor element with a vibration sensitive component, such as a membrane, wherein the sensor element is connected to the container body in such a way that the vibration sensitive component reacts to vibrations of the container body. The vibrational response of the food material is then measured by measuring the displacement of the vibration sensitive component of the sensor element. Such a sensor element can be securely attached to a pipe or a tube in a production or processing line, without any coupled oscillations, and allows for a local measurement of the food material texture.

BRIEF DESCRIPTION OF THE DRAWINGS

Hereinafter non-limiting examples and experimental results are explained with reference to the drawings, in which.

DETAILED DESCRIPTION OF CURRENTLY PREFERRED EMBODIMENTS

Figure 1:
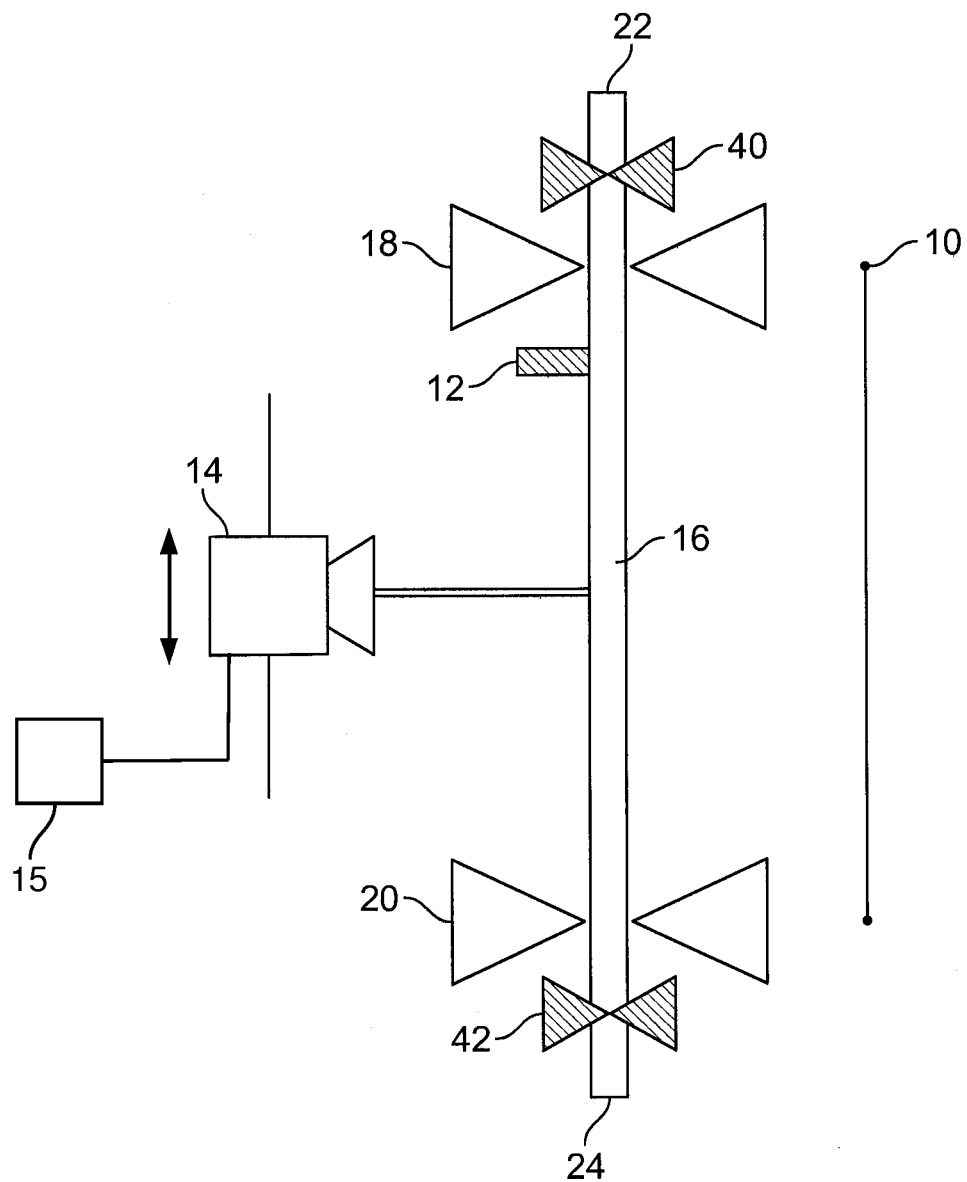
FIG. 1 shows an apparatus for determining the texture of food material according to a first embodiment.

FIG. 1 shows an apparatus 10 for determining the texture of food material according to a first preferred embodiment. The food material to be investigated is contained within a tube 16, made of stainless steel. The apparatus 10 can be operated in an off-line mode, where the food material is stationary in the tube 16, or an on-line mode. In the former case, the food material is isolated from external influences by closing an upper valve 40 and a lower valve 42 which are incorporated in the tube 16. In the latter case, the valves 40, 42 are opened and the food material is in flow through the apparatus length, entering the tube 16 through a mass inlet 22 and leaving the tube 16 through a mass outlet 24. The tube 16 may be for example part of a production or processing line. The tube 16 is secured in two places along its length with an upper 18 and a lower 20 bearing and made to oscillate in a direction perpendicular to its long axis by using a piezo actuator 12. The oscillating part of the tube 16 is the region between the two bearings 18, 20. The displacement of the tube 16 is measured with a conventional vibrometer 14 which is positionable at different places along the apparatus 10 due to the nature of the response waves caused by texture differences between the used food materials. Piezo actuator 12 and conventional vibrometer 14 are coupled via a PC board (not shown). In a measurement procedure, a plurality of vibrational impacts with varying frequencies can be applied to the tube 16, using the piezo actuator 12, and the resulting tube displacement for every impact can be measured with the vibrometer 14. An analyser unit 15 (not shown) then determines the frequency and magnitude of the tube oscillations for every applied vibrational impact. In this way, a frequency-magnitude profile of the food material oscillations is provided for a given set of outer parameters, such as pressure, temperature, position in the production line, point of impact (i.e., the position where the vibrational impact is applied), shape and size of the food container etc. Any change in food material texture that may be caused by a change of the outer parameters or by interaction of the food material with its environment (e.g., cooling down of the material by heat exchange with the surroundings) is reflected in the corresponding frequency-magnitude profile, which can thus be used to detect such changes in the food material properties.

Figure 2:
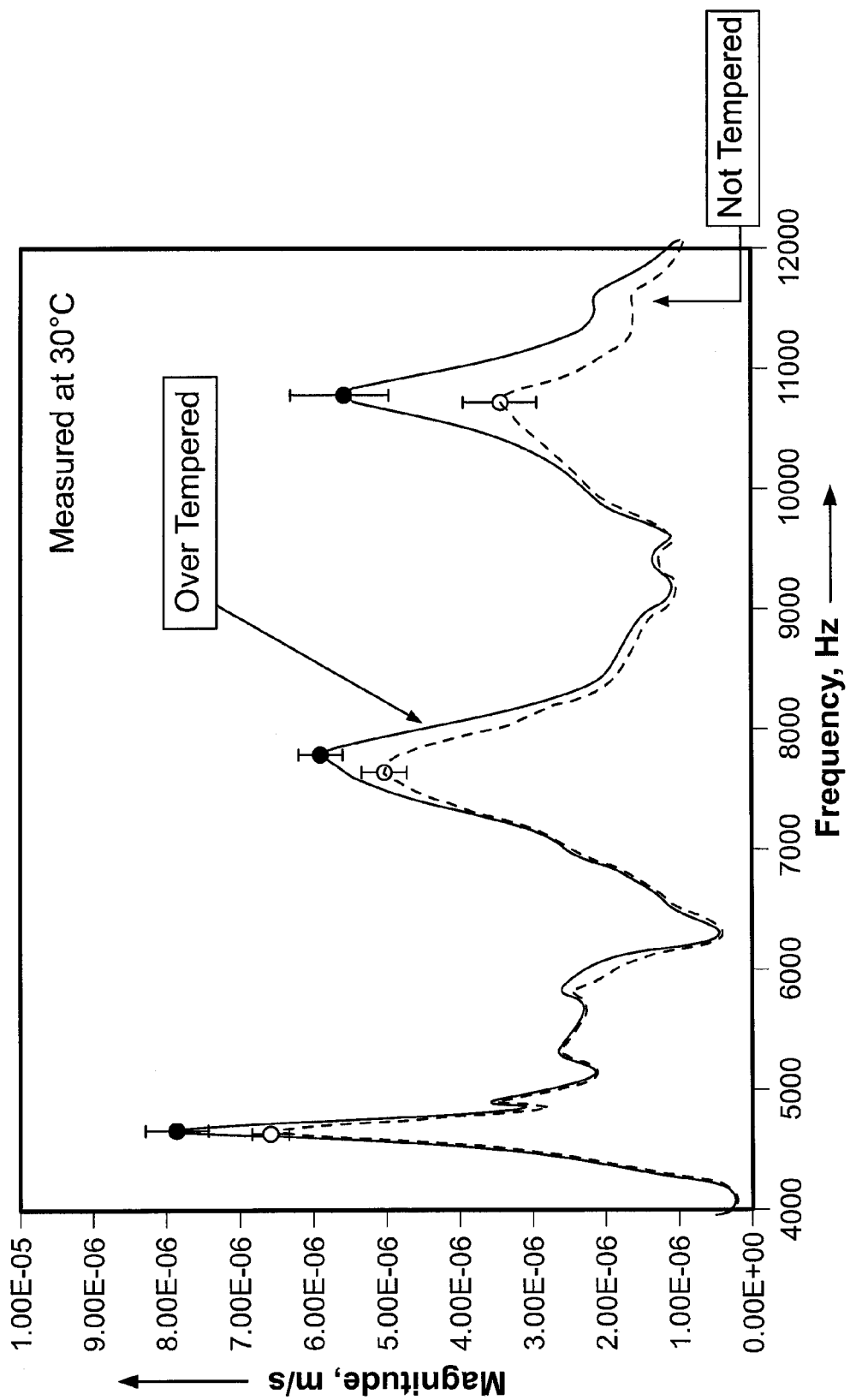
FIG. 2 shows a plot of oscillation magnitude vs. oscillation frequency for the vibrational response of over-tempered and untempered chocolate at identical temperature, measured with the apparatus according to the first embodiment.

FIG. 2 shows characteristic frequency-magnitude plots for over-tempered and untempered chocolate mass that were measured at identical temperatures under isothermal conditions, using the above described apparatus 10 in the off-line mode. The plots reveal a clear difference between the oscillation profiles of the chocolate mass measured as a sample with different thermal and shearing history that is most pronounced around the centres of the resonance peaks. While all peaks show a distinct change in peak height between the two sample stages, a shift in peak position is also observed between the two peaks at about 7700 and about 7800 Hz, respectively. Thus, a comparison of the two plots (or the underlying data or sensor output) allows for a clear distinction between over-tempered and untempered chocolate material. If the coarse position of at least one of the resonance peaks is known for a given food material, a change in texture can also be identified by a single measurement at a frequency close to the centre of that peak. If it has to be determined, for example, whether, for a given set of outer parameters, a chocolate material is tempered or not, it suffices to determine the oscillation magnitude of the chocolate mass with identical temperature at around, for example, 10800 Hz (see FIG. 2). In this way, variations in food material texture can be identified in a quick, reliable and uncomplicated manner without destroying or even disturbing the investigated material.

Figure 3:
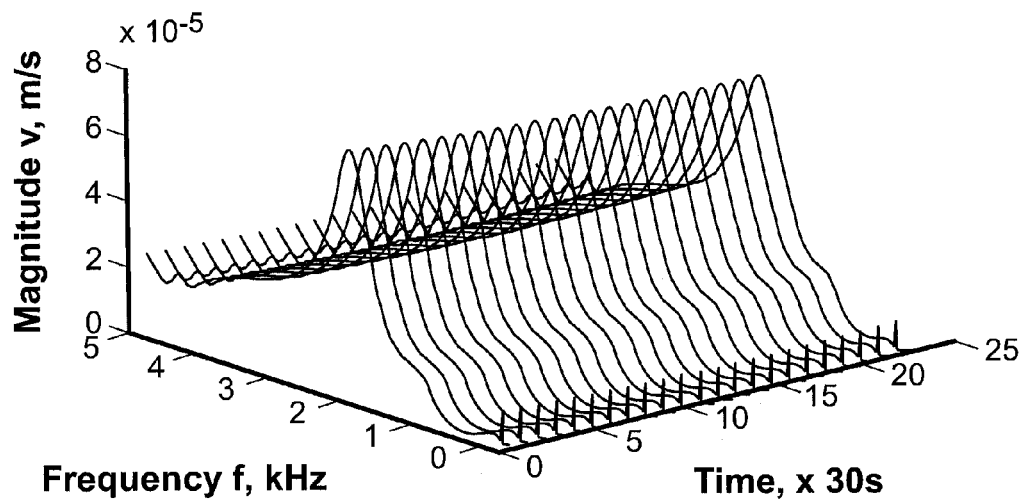
FIGS. 3 and 4 show plots of oscillation magnitude vs. oscillation frequency and time for the vibrational response of not pre-crystallised and pre-crystallised chocolate, respectively, at identical temperature, measured with the apparatus according to a second embodiment.
Figure 4:
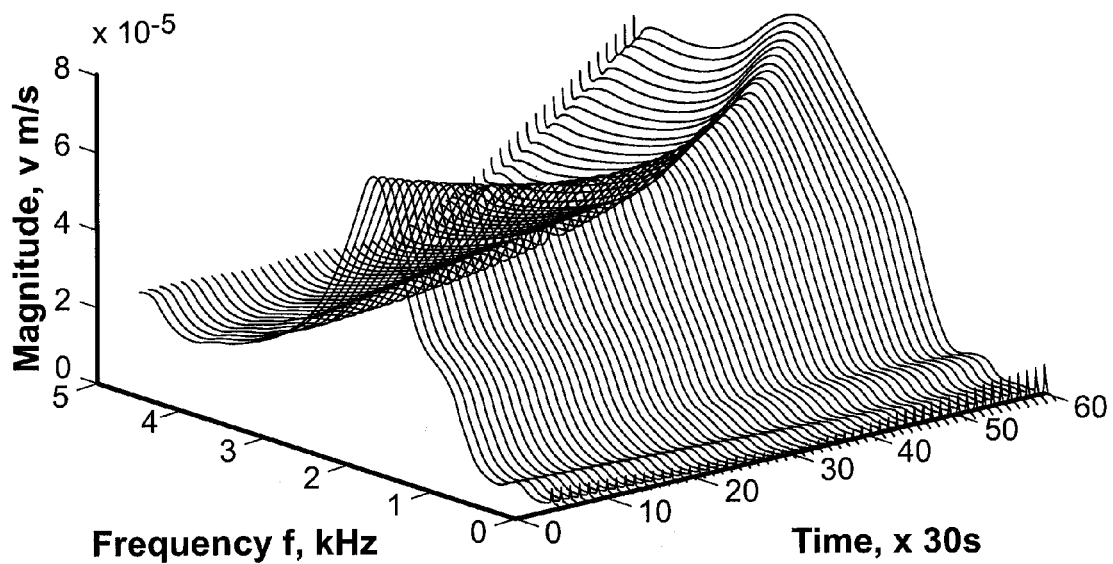

FIGS. 3 and 4 show frequency-magnitude-time plots for not pre-crystallised and pre-crystallised chocolate, respectively, that were measured at an identical temperature (28° C.) in time steps of 30 s, using the apparatus 10 of a second embodiment (described below and shown in FIG. 5) in the off-line mode, i.e., both samples did not flow in the tube during the measurement. Such plots can be used to monitor the solidification process of liquid or semi-solid food materials, providing important information on the material texture properties. In the examples shown in FIGS. 3 and 4, the only difference between the two chocolate materials is the presence of a crystalline structure due to a different thermal history in the chocolate material for which the plot is shown in FIG. 4. This difference has a significant impact on the solidification behaviour of the two materials that is mirrored in the corresponding plots. While the frequency-magnitude plot for the not pre-crystallised chocolate mass remains almost unchanged with time (FIG. 3), a clear change in peak height is observed both at about 2 and at about 5 kHz for the pre-crystallised chocolate mass (FIG. 4) on the investigated timescale, reflecting the phase transition of the material. On the one hand, this data (in particular FIG. 4) shows that the method of the invention provides an effective and sensitive tool for monitoring phase transitions and structural changes in liquid and semi-solid food materials. On the other hand, the examples of FIGS. 3 and 4 demonstrate that the investigation of the solidification behaviour of a given food sample yields information on the structural details and thermal history of the sample. Hence, the present method can be employed to determine the structure of a food material in advance, before the material has fully solidified, thus providing a valuable quality test, e.g., during the production process. As shown in FIGS. 3 and 4, the frequency-magnitude plots of the two chocolate materials show resonance peaks at about 2 and about 5 kHz. Generally speaking, the detection of a well-defined vibrational response of the investigated chocolate material is an unexpected finding due to the high level of inhomogeneities and the low concentration level of involved fat share (~1% of fat phase becomes solid during conventional tempering) this system exhibits. In particular, the observation of resonance modes at such low frequencies is surprising, since resonance peaks are commonly expected to occur at higher frequencies up to the ultrasound range for this type of material. However, as demonstrated in the data presented in FIGS. 2 to 4, it is fully sufficient for the present method, to perform the measurements at frequencies below 20 kHz, preferably even below 10 kHz. This frequency range is easily accessible with conventional measurement equipment, so that the set up cost can be kept at a reasonably low level and the risk of disturbing or damaging the food material during the measurement is minimised.

Figure 5:
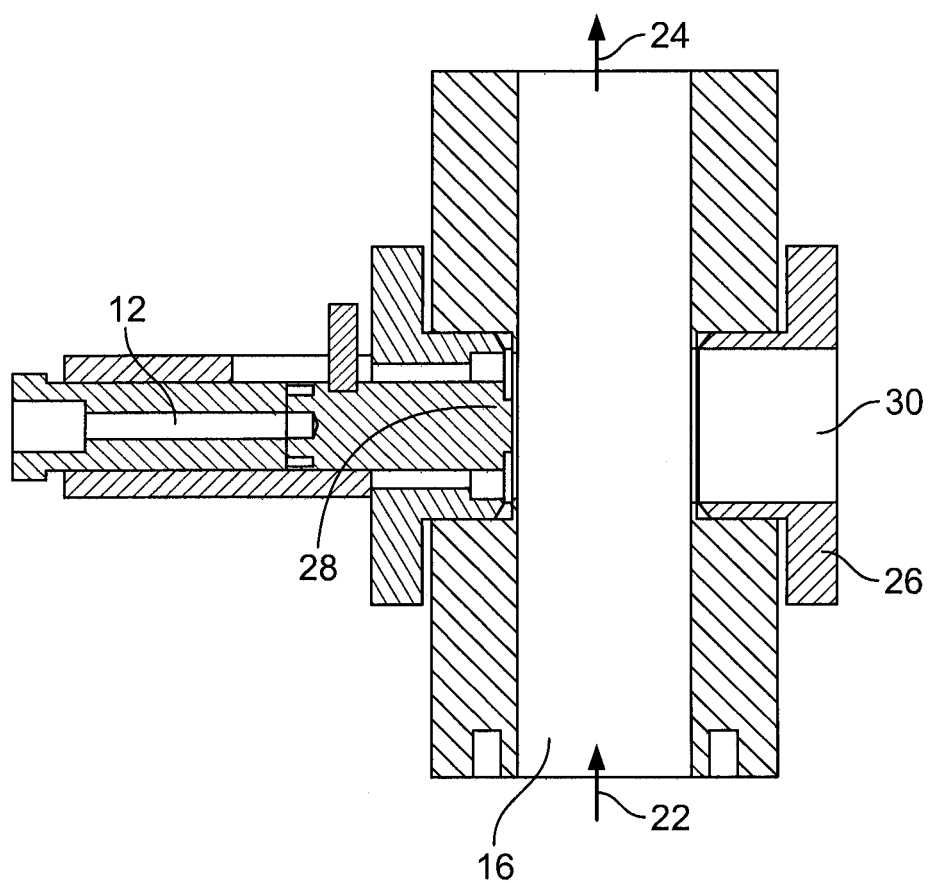
FIG. 5 shows part of an apparatus for determining the texture of food material according to a second embodiment, including a sensor element.

FIG. 5 shows part of an apparatus 10 for determining the texture of food material according to a second preferred embodiment. Similar to the case of the first preferred embodiment described above, the food material is contained within a tube 16, where it may be stationary (off-line mode) or in flow through the apparatus 10 (on-line mode) via the mass inlet 22 and outlet 24. Further, the apparatus 10 also comprises a piezo actuator 12 and a vibrometer (not shown here). In addition, the apparatus 10 of the second embodiment contains a sensor element 26 that surrounds the tube 16 and is secured to it. Two membranes 28, 30 are attached to the sensor element 26 in a way that they are movable in a direction perpendicular to the length of the tube 16 over a preset distance. A vibrational impact is applied to the tube 16 via the first membrane 28, by using the piezo actuator 12. The resulting oscillations of the tube 16 cause the second membrane 30 to oscillate with the same frequency and magnitude as the tube 16 itself and the tube oscillations can thus be quantified by measuring the oscillations of the second membrane 30 with the vibrometer (not shown). The oscillating part of the tube 16 is substantially defined by the diameter of the parts of the membranes 28, 30 that are in contact with the tube 16. The sensor element 26 can be attached to tubes 16 or pipes at different positions in a production or processing line, without any coupled oscillations, and allows for a local measurement of the food material texture. The sensor element 26 is preferably made of a metal, such as stainless steel, so as to exhibit a high level of thermal conductivity. Hence, a heating or cooling device (such as an electrical heater or a cooled heat exchanger, not shown) may be connected to the sensor element 26, so that the temperature of the investigated food material can be varied and the effect of temperature on the food material texture can be studied. Such a set up is particularly useful for the detailed investigation of solidification processes, for example after the procedure of tempering chocolate.

Figure 6:
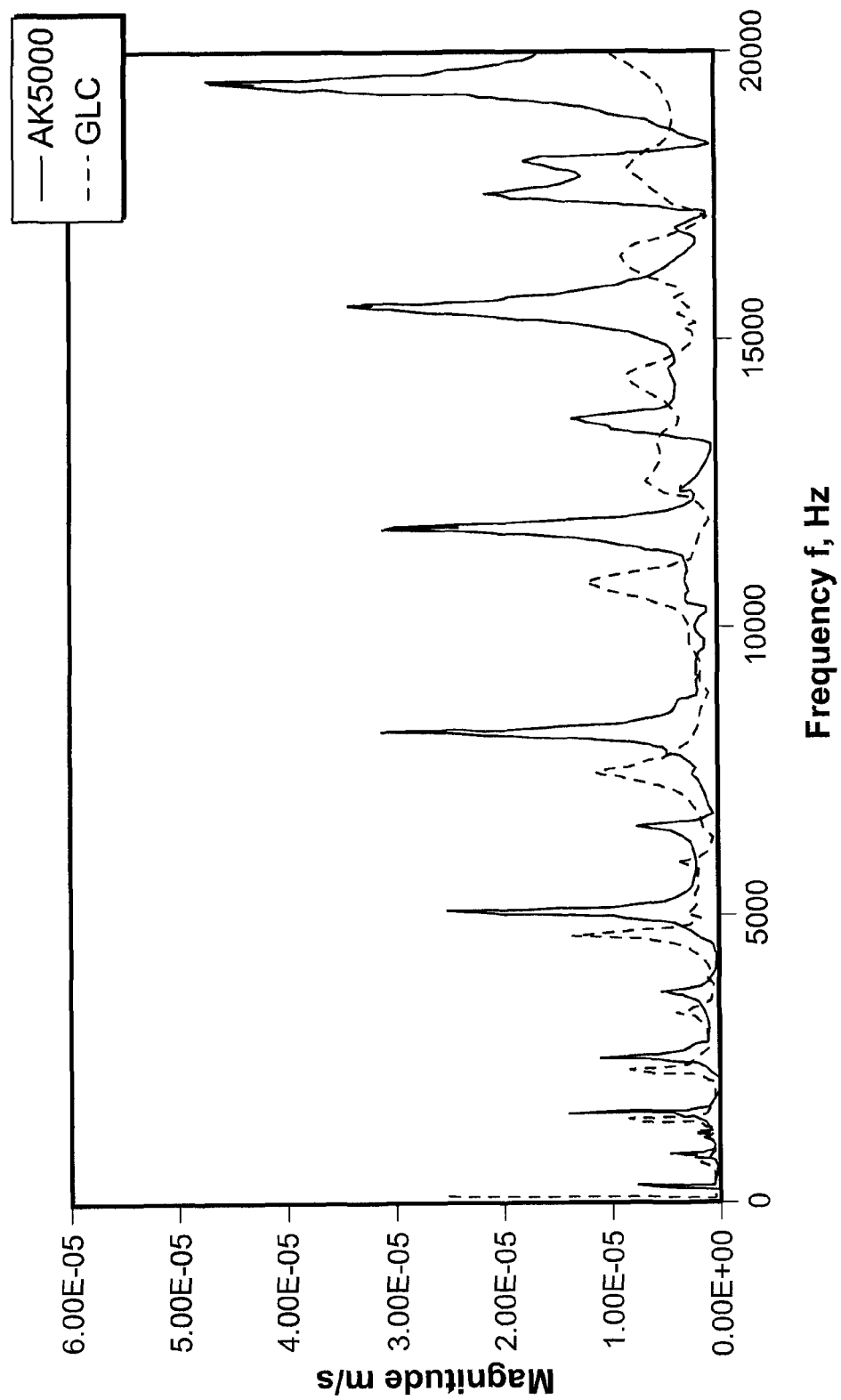
FIG. 6 shows a plot of oscillation magnitude vs. oscillation frequency for the vibrational response of a silicone oil (AK 5000) and a glucose solution (GLC) measured with the apparatus according to the first embodiment.

FIG. 6 shows a plot of oscillation magnitude vs. oscillation frequency for the vibrational response of a silicone oil (AK 5000; Wacker-Chemie GmbH) and a glucose solution (GLC) measured with the apparatus according to the first embodiment of the invention. The silicone oil and the glucose solution have identical viscosities (4.42 Pas) but different densities (950 g/l for AK 5000 and 1353 g/l for GLC). As can be seen from FIG. 6, the plots of the two measured materials differ significantly in peak magnitude and frequency. The measurement method of the invention is sensitive to differences in chemical composition and molecular structure of the investigated system and can be applied to detect even small changes in texture that occur on a microscopic (molecular) level. In particular, as FIG. 6 shows, these changes in texture do not necessarily have to be related to different viscosity, but may be related, e.g., to different density. The same can be expected for different crystalline structures, molecular structures etc.

The invention claimed is:

1. An apparatus for determining texture characteristics of a food material having variable textural characteristics wherein the food material is in a liquid or a semi-solid state, said apparatus comprising:
    a device for generating a plurality of vibrational impacts with varying predetermined frequencies to a test sample of the food material, wherein each vibrational impact has a frequency within a predetermined frequency range and a predetermined time-interval,
    a device for measuring a plurality of experimental vibrational responses of the test sample of the food material to the plurality of vibrational impacts,
    a container for holding the test sample during both the generating of the vibration impacts and the measurement of the experimental vibrational responses of the test sample, and
    an analyzer for comparing the plurality of experimental vibration responses of the test sample with a plurality of reference vibration responses determined using a calibration sample of the food material having known textural characteristics, thereby determining the textural characteristics of the test sample,
wherein the container is a process pipe included in a de-aeration process line for manufacture of the food material, and wherein the determination of textural characteristics of the test sample is used to monitor the de-aeration process line.

2. The apparatus according to claim 1, wherein the generating device is a piezo actuator and measuring device is a vibrometer.

3. The apparatus according to claim 1, wherein the plurality of vibrational impacts are applied to the process pipe, and wherein the plurality of experimental vibrational responses of the test sample are measured using displacement of the process pipe.

4. The apparatus according to claim 1, wherein the food material is chocolate or a chocolate-containing food product.

5. The apparatus according to claim 1, wherein the food material is stationary in the process pipe during the determination of the textural characteristics of the test sample.

6. The apparatus according to claim 1, wherein the food material is flowing in the process pipe during the determination of the textural characteristics of the test sample.

7. The apparatus according to claim 1, wherein flow direction of the food material in the process pipe is substantially perpendicular to the plurality of vibrational impacts and to the plurality of measured experimental vibrational responses of the test sample.

8. The apparatus according to claim 1, wherein the predetermined frequency range is equal to or less than 20 kHz.

9. The apparatus according to claim 1, wherein the predetermined frequency range is equal to or less than 10 kHz.

10. An apparatus for determining texture characteristics of a food material having variable textural characteristics, said apparatus comprising:
a device for generating a plurality of vibrational impacts with varying predetermined frequencies to a test sample of the food material, wherein each vibrational impact has a frequency within a predetermined frequency range and a predetermined time-interval,
a device for measuring a plurality of experimental vibrational responses of the test sample of the food material to the plurality of vibrational impacts,
a container for holding the test sample during both the generating of the vibration impacts and the measurement of the experimental vibrational responses of the test sample, the container being a process pipe, and
an analyzer for comparing the plurality of experimental vibration responses of the test sample with a plurality of reference vibration responses determined using a calibration sample of the food material having known textural characteristics, wherein the analyzer determines the resonant mode frequencies and magnitudes of the test sample and uses the resonant mode frequencies and magnitudes, along with the experimental vibrational responses, of the test sample to determine the textural characteristics of the test sample.

11. The apparatus according to claim 10, wherein the plurality of vibrational impacts are applied to the process pipe, and wherein the plurality of experimental vibrational responses of the test sample are measured using displacement of the process pipe.

12. The apparatus according to claim 10, wherein the food material is chocolate or a chocolate-containing food product.

13. The apparatus according to claim 10, wherein the food material is stationary in the process pipe during the determination of the textural characteristics of the test sample.

14. The apparatus according to claim 10, wherein the food material is flowing in the process pipe during the determination of the textural characteristics of the test sample.

15. The apparatus according to claim 10, wherein flow direction of the food material in the process pipe is substantially perpendicular to the plurality of vibrational impacts and to the plurality of measured experimental vibrational responses of the test sample.

16. The apparatus according to claim 10, wherein the predetermined frequency range is equal to or less than 20 kHz.

17. The apparatus according to claim 10, wherein the predetermined frequency range is equal to or less than 10 kHz.

* * * * *